United States Patent [19]

Takeyasu et al.

[11] 4,255,762
[45] Mar. 10, 1981

[54] APPARATUS FOR INSPECTING PIPES IN A PLANT

[75] Inventors: Kiyoo Takeyasu, Tokorozawa; Kanji Kato, Kokubunji; Tatsuo Goto, Hamura; Yoozoo Oouchi, Kokubunji; Kazuhiro Yoshida, Hitachi; Yoshitoshi Ito, Oume; Katsumi Takami, Tokyo, all of Japan

[73] Assignee: Hitachi, Ltd., Tokyo, Japan

[21] Appl. No.: 56,853

[22] Filed: Jul. 12, 1979

[30] Foreign Application Priority Data

Jul. 26, 1978 [JP] Japan .................................. 53-90466
Jul. 26, 1978 [JP] Japan .................................. 53-90467

[51] Int. Cl.³ .............................................. H04N 7/18
[52] U.S. Cl. .................................... 358/100; 358/210
[58] Field of Search .................... 356/241; 358/98, 99, 358/100, 101, 108, 210, 93, 106, 903; 318/567, 569, 575, 576, 577

[56] References Cited

U.S. PATENT DOCUMENTS

| | | | |
|---|---|---|---|
| 3,764,736 | 10/1973 | Kosky et al. ......................... | 358/100 |
| 3,906,324 | 9/1975 | Smith ................................... | 318/567 |
| 4,021,840 | 5/1977 | Ellsworth et al. .................. | 358/100 |

Primary Examiner—Benedict V. Safourek
Assistant Examiner—Joseph A. Orsino, Jr.
Attorney, Agent, or Firm—Craig and Antonelli

[57] ABSTRACT

Apparatus for inspecting pipes in a plant, comprising an elongate inspection head portion which is provided with an optical system for receiving an inspection image by approaching an inner surface of a pipe being an object to-be-inspected; at least one proximity sensor which is disposed in the inspection head portion in order to detect a relative distance between the inspection head portion and the proximate object; a positioning mechanism which consists of a plurality of driving shafts for advancing or retreating, rotating, and revolving the inspection head portion; a control device which is capable of programmed operation and which drives and controls the positioning mechanism in a predetermined operation sequence programmed in advance; a data storage device which stores positional data of the respective driving shafts of the positioning mechanism; and an image processor which is disposed at a position remote from the inspection head portion and which reconstructs the inspection image from video signals; the control device controlling the positioning mechanism on the basis of an output signal from the proximity sensor, so that the inspection head portion can be moved and controlled from an initially-set position outside the pipe towards an inspection position of the pipe without contacting with the object to-be-inspected.

8 Claims, 18 Drawing Figures

APPARATUS FOR INSPECTING PIPES IN A PLANT

FIELD OF THE INVENTION

This invention relates to apparatus for inspecting pipes. More particularly, it relates to the construction of inspection apparatus suitable for the inspection of pipes in a large-sized plant wherein the surfaces to-be-inspected of the pipes are visually inspected at a remote spot, and also to a method of controlling the inspection apparatus.

DESCRIPTION OF THE PRIOR ART

In general, a large-sized plant such as liquid storage tank and nuclear reactor has various kinds of pipes disposed therein.

Such plant is subjected to a routine inspection in order to secure safety. In this case, in order to protect an operator from a poisonous gas or contamination due to a radioactive substance, it is desirable that the various sorts of pipes can be automatically and promptly inspected at a remote position safe for the operator.

To this end, in the inspection of e.g. the nuclear reactor, a mount is installed on the upper part of the reactor after removing some of structures in the reactor, an apparatus for inspection is transported into the reactor by means of a traverse machine attached to the mount, and the interior of the pipe is inspected with the inspection apparatus by the automatic control or by the remote control by the operator.

Inspection contents for the nuclear reactor include several sorts, and one important among them is the visual inspection. In this inspection, an inspection apparatus provided with a TV camera is employed, and an inspection head provided with an optical system for receiving an image is moved in the pipe, whereby the appearance of the wall of the pipe is projected on a monitor TV set lying at a remote spot.

In such large-sized plant, however, many sorts of pipes having unequal bores are objects to-be-inspected. In some cases, the pipe has another pipe or the like at its inlet, and the latter becomes an obstacle to the insertion of the inspection head into the former.

Therefore, it has heretofore been common practice to design a plurality of kinds of inspection heads having different shapes and structures in conformity with the objects to-be-inspected and to adopt a system wherein the inspection heads are exchanged in accordance with the objects to-be-inspected as described in e.g. Japanese Published Unexamined patent application No. 127,094/1975 or a system wherein many sorts of inspection heads are collectively carried on a traverse machine and are properly used in dependence on the objects to-be-inspected as described in e.g. Japanese Published patent application No. 5872/1977. However, the former system has had the problem that the period of time for the inspection work increases, and the latter system the problem that the apparatus becomes large in size.

In the prior-art apparatus, a pipe wall contactor is disposed at the fore end of the inspection head to be inserted into the pipe, and the object is imaged while holding the TV camera at a fixed distance from the pipe wall by means of the contactor. Therefore, it has sometimes been the case that the trace of the contactor left on the pipe wall hinders the visual detection of flaws.

SUMMARY OF THE INVENTION

This invention has been made in order to solve such problems of the prior arts, and has for its object to provide inspection apparatus which can execute the visual inspections of many kinds of pipes with a single inspection head.

Another object of this invention is to provide apparatus capable of executing such visual inspections without contact with many kinds of pipes.

Still another important object of this invention is to provide apparatus and a control method therefor with which a visual inspection of high precision is possible even when the setting of inspection apparatus into front of a pipe by a traverse machine deviates from a predetermined position.

In order to accomplish the objects, the inspection apparatus according to this invention comprises:

an inspection head portion which is provided with an optical system for receiving an image of an inner surface of the pipe being an object to-be-inspected, means for converting the inspection image received into said optical system, into electrical video signal, at least one proximity sensor which is disposed in said inspection head portion in order to detect a relative distance between said inspection head portion and the proximate object, a positioning mechanism which is made up of a plurality of driving shafts for moving said inspection head portion, control means capable of programmed operation, for guiding said inspection head portion from an initially set position outside the pipe to an inspection position inside said pipe and moving said inspection head portion along a track set with reference to the object to-be-inspected and without contact with said object to-be-inspected, and for driving said positioning mechanism in a predetermined operation sequence programmed in advance in response to an output signal from said proximity sensor, and image processing means situated at a position remote from said inspection head portion and for reconstructing the inspection image from the video signals.

The positioning mechanism has a first driving shaft which is elongate and which is movable in the direction of the center axis of the pipe, a second driving shaft which moves the first driving shaft in the direction orthogonal to the center axis, and a third driving shaft which intersects orthogonally to the second driving shaft and which revolves this driving shaft, the inspection head portion being located at a fore end part of the first driving shaft.

In accordance with the method of controlling inspection apparatus according to this invention, the inspection apparatus set into front of a pipe being an object to-be-inspected by means of a traverse machine is controlled by:

the step of advancing a first driving shaft to insert an inspection head into the pipe, the step of revolving a third driving shaft a predetermined angle while moving a second driving shaft in response to an output of a proximity sensor so as to hold constant a distance between the inspection head and an inner surface of the pipe, thereby to detect a positional deviation between the third driving shaft and the center axis of the pipe, and the inspection image input step of controlling the revolution angle of the third driving shaft in dependence on the positional deviation while moving the second driving shaft in response to the output of the proximity sensor, thereby making it possible to pick up inspection images at positions at equal intervals in the circumferential direction of the pipe.

Further, in accordance with this invention, the first driving shaft of the positioning mechanism is made rotatable, and the amount of rotation of the first driving shaft is controlled in dependence on the amount of positional deviation between the third driving shaft and the center axis of the pipe and the amount of revolution of the third driving shaft, whereby the optical system of the inspection head always faces perpendicularly to the inner surface of the pipe at various inspection positions.

The foregoing and other objects, advantages, manner of operation and novel features of the present invention will be understood from the following detailed description when read in connection with the accompanying drawings.

DESCRIPTION OF THE PREFERRED EMBODIMENTS

Figure 1:
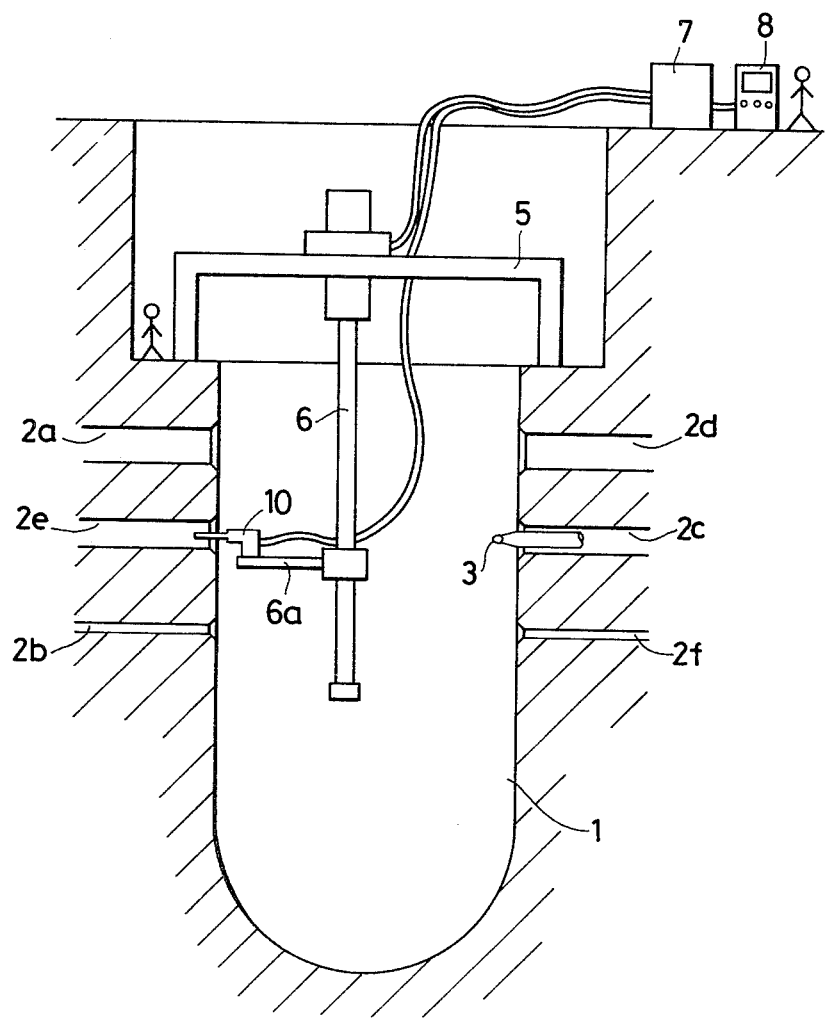
FIG. 1 is a view showing an example of a plant which is an object to be inspected by the inspection apparatus of this invention.

FIG. 1 shows the schematic construction of a nuclear reactor which is one of objects to-be-inspected in this invention. Numeral 1 designates the reactor, and numerals 2 (2a-2f) designate various pipes which are installed around the reactor 1. In case of the inspection, after removing some of structures in the reactor, a mount 5 is installed over the reactor and a traverse machine 6 is attached thereto.

The traverse machine 6 carries an inspection apparatus 10 provided with a TV camera, and moves it into front of each pipe. Thereafter, the inspection apparatus executes a predetermined inspection work.

A video signal from the TV camera is transmitted to a monitor TV set 8 situated at a remote spot, and is observed by an operator. On the other hand, the traverse machine 6 and the inspection apparatus 10 are controlled by a control device 7 which are also located at the remote spot.

Figure 2:
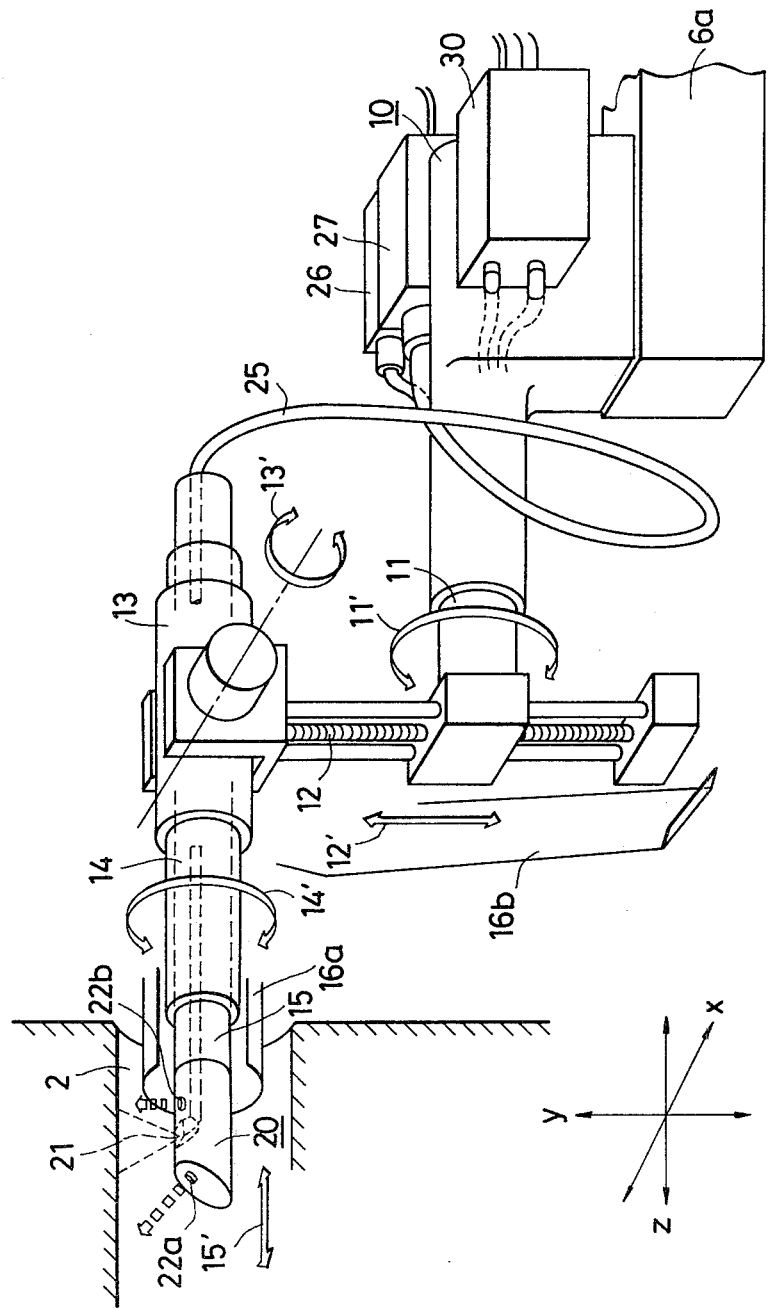
FIG. 2 is a view showing the whole construction of the inspection apparatus which is an embodiment of this invention.

Shown in FIG. 2 is the construction of a mechanism portion of the inspection apparatus of this invention suitable for the visual inspection of many kinds of pipes. In the figure, numeral 2 indicates a pipe which is an object to-be-inspected, and symbol 6a indicates that end of the traverse means 6 which carries the inspection mechanism portion 10 and which serves to roughly set it to the position in front of the pipe, the end being a part outside the scope of this invention. To the end of inspecting the inner surfaces of many kinds of pipes having different diameters, the inspecting mechanism portion has five degrees of freedom in correspondence with thick arrows 11'-15' as follows. It is provided with a sliding shaft 15 which moves an inspection head 20 in the axial direction of the pipe, a shaft 14 which rotates the sliding shaft 15, a swinging shaft 13 which alters the inclination angle of a part including the shafts 14 and 15, a shaft 12 which extends or shortens a part including the above-mentioned shafts, and a shaft 11 which revolves the whole structure stated above. However, one or more of these driving shafts can be omitted for some kinds of object pipes or under some job conditions. On the other hand, the inspection head 20 at the fore end has arranged thereon an optical system for an image 21 which illuminates the object surface and which receives the image of the surface, and proximity sensors 22a and 22b which function to detect the relative distances between the inspection head and the object surface. The input from the imaging optical system is transmitted to an ITV camera 27 through an image guide, and is further offered as a video information to the operator who monitors the monitor TV set at the remote spot is indicated at 8 in FIG. 1. A flexible member 25 contains, besides the image guide therefor, a light guide or the like for feeding the inspection head with illumination light from a light source unit 26.

The fact that such construction is suitable for the visual inspection of many kinds of pipes will be described with reference to FIGS. 3(a)-3(c).

Figure 3A:
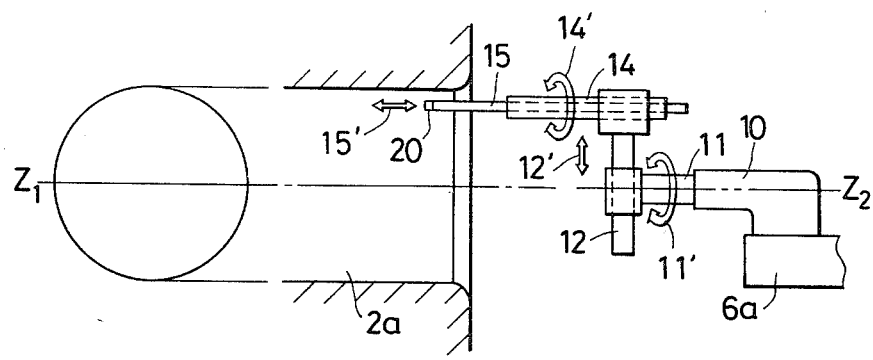
FIGS. 3(a)-3(c) are views for explaining examples of structures of pipes in a plant to-be-inspected and states of inspection works by the apparatus of this invention.

FIG. 3(a) shows a situation of inspection for the pipe 2a having a large diameter. In this case, the scanning of the inspection head 20 in the circumferential direction can be executed by the revolving shaft 11, and the scanning in the axial direction by the sliding shaft 15. At this time, if the center axis of the pipe 2a indicated by a one-dot chain line $Z_1$ and the reference axis of the inspection apparatus 10 indicated by a two-dot chain line $Z_2$ are not coincident, the relative distance between the inspection head 20 and the object surface can be made a fixed value by controlling the extending or shortening shaft 12. Further, in case where the relative angle between the inspection head and the object surface deviates from a predetermined angle on account of the non-coincidence, it can be corrected by the rotating shaft 14.

Figure 3B:
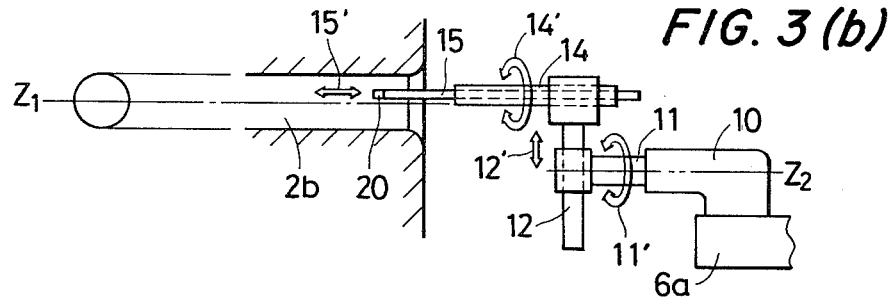

FIG. 3(b) shows a situation of inspection of the pipe 2b having a small diameter. In this case, unlike the case of FIG. 3(a), the scanning in the circumferential direction is executed by the rotating shaft 14, and the control for keeping constant the relative distance between the object surface and the inspection head 20 is executed by the complex motion of the revolving shaft 11 and the extending or shortening shaft 12.

Figure 3C:
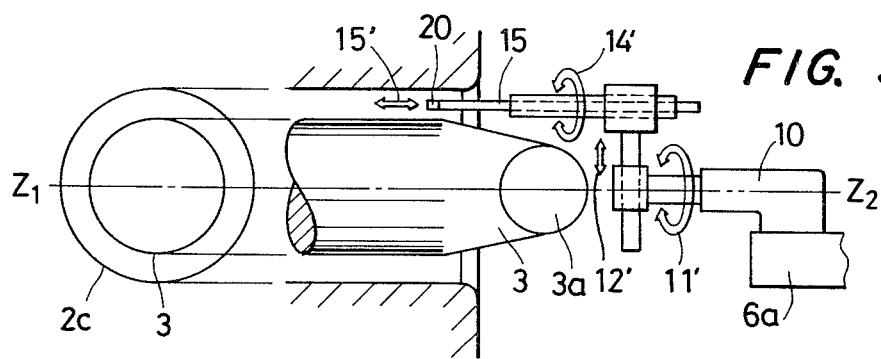

FIG. 3(c) shows a situation of inspection for the pipe 2c in which a cylindrical structure 3 is installed. In this case, conditions for utilizing the shafts are basically the same as in the case of FIG. 3(a). However, owing to the construction in which the sliding shaft 15 is arranged at the foremost end of the mechanism portion, the inspection work can be executed under the condition under which a protuberance 3a of the structure 3 is avoided. Moreover, the inspection head 20 can be inserted in a narrow gap portion defined by the structure 3 and the pipe 2 in such a way that the sliding shaft 15 to which the inspection head 20 is attached is designed fine.

On the other hand, in all the cases of FIGS. 3(a)-3(c), when a relative inclination has occurred between the center axis $Z_1$ of the pipe and the reference axis $Z_2$ of the inspection apparatus, it can be corrected by controlling the swinging shaft 13 shown in FIG. 2.

As described above, the feature of the inspection mechanism according to this invention resides in that the direct-acting extending-and-shortening shaft 12 is arranged at the stage succeeding to the revolving shaft 11, that the rotating shaft 14 which rotates about the axis orthogonal to the extending-and-shortening shaft 12 is arranged at the stage succeeding to the shaft 12, and that the sliding shaft 15 which directly acts in the direction parallel to the center axis of the rotating shaft 14 is arranged, the inspection head 20 being disposed at the fore end of the sliding shaft 15, whereby even the object having the structure within the pipe can be inspected besides the large number of kinds of pipes having unequal diameters.

Figure 4A:
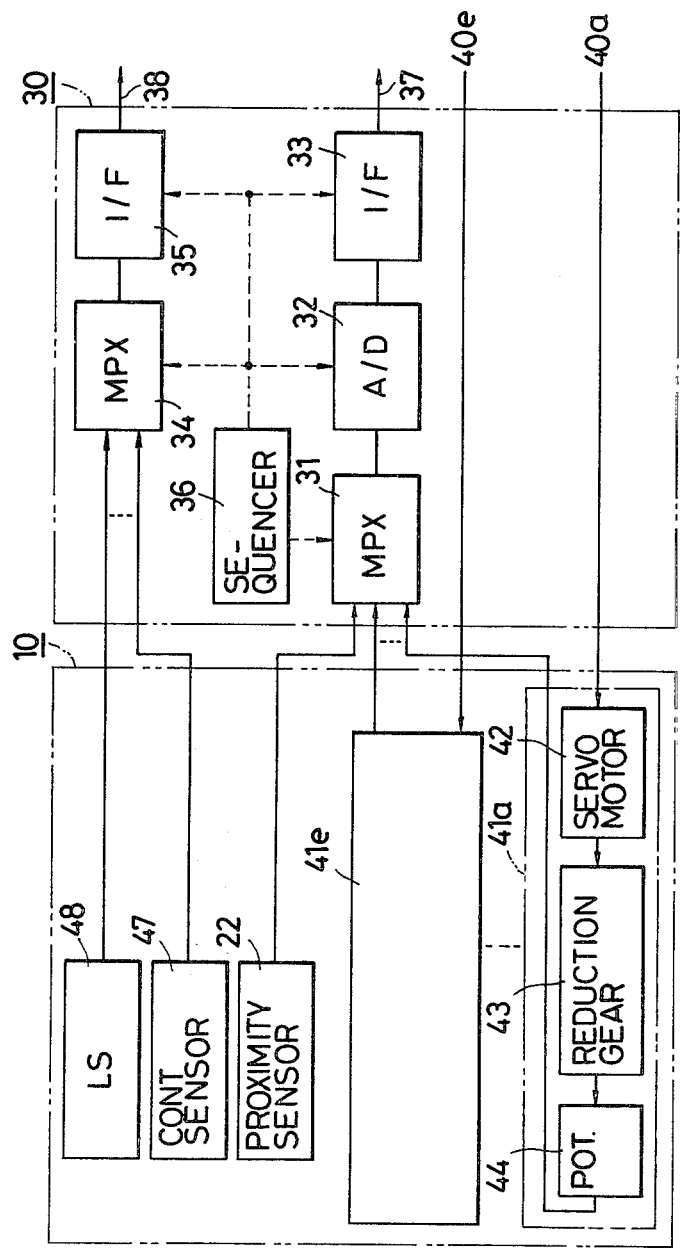
FIGS. 4(a) and 4(b) are diagrams showing the whole construction of a control device in the inspection apparatus according to this invention.
Figure 4B:
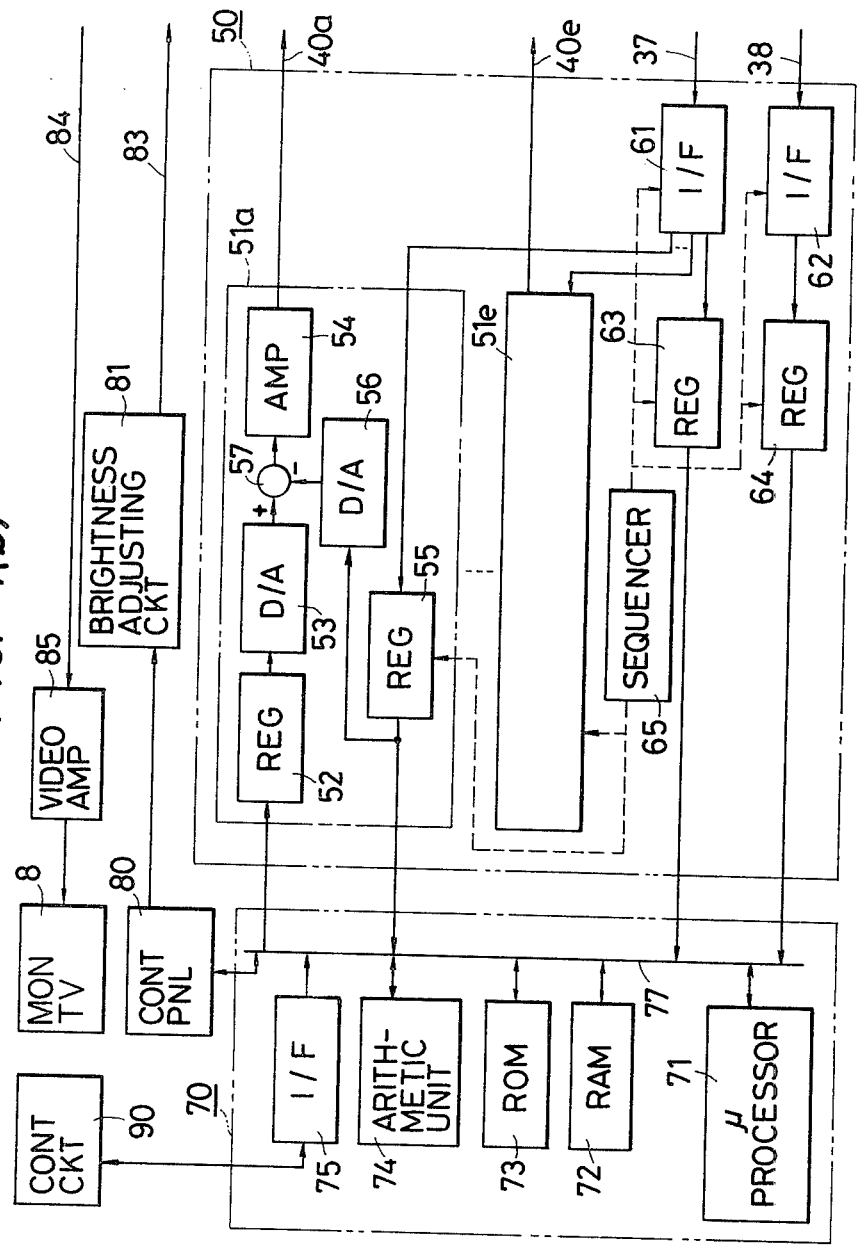

Shown in FIGS. 4(a) and 4(b) is an embodiment of a control circuit which serves to scan the inspection head along the inner surface of the pipe by employing the visual inspection mechanism stated above.

Referring to FIG. 4(a), numeral 10 designates the inspection mechanism portion, in which numerals 41 (41a-41e) indicate parts for driving the various shafts 11-15, and each of the parts is constructed of, for example, a d.c. servomotor 42, a reduction gear 43 and a potentiometer 44 as a position detector. Actually there are five systems of drive portions corresponding to the motions of the five sorts of driving shafts 11-15 shown in FIG. 2, but for the sake of brevity the connections of signals are illustrated with the part 41a as a typical example. In the inspection mechanism, there are further arranged the proximity sensor 22, a contact sensor 47, a limit switch 48, etc. Among them, the contact sensor 47 is disposed in a manner to be accessory to, for example, an apparatus protective cover 16a or 16b shown in FIG. 2, and it generates a signal when the inspection mechanism has touched, for example, the object surface due to any malfunction. The limit switch 48 generates a signal when the driving portion 41 has moved up to the limit of its operating range. Although each of the proximity sensor, the contact sensor and the limit switch is shown in the number of one for the brevity sake in the drawing, it is actually arranged in a larger number as may be needed.

The control of such inspection mechanism portion 10 is made by the control device 7 which lies at the spot considerably remote from the inspection position as also illustrated in FIG. 1. However, when a method is resorted to wherein output signals from the large number of potentiometers 44, limit switches 48 or sensors 22, 47 above described are transmitted to the remote spot as they are, connection cables become a very large scale. It is accordingly desirable to serialize these outputs and to transmit the serialized signals with a small number of transmission lines. To this end, a pre-processing circuit portion shown at 30 in FIG. 2 or FIG. 4(a) is arranged near the inspection mechanism portion 10.

In case of the embodiment illustrated in FIG. 4(a), two channels of transmitters are disposed in the pre-processing circuit portion 30. First, in case of signals such as of the potentiometer 44 and the proximity sensor 22 the output levels of which vary according to circumstances, they are transmitted in series on a signal transmission line 37 and in the form of digital signals by the use of a multiplexor 31, an A/D converter 32 and a transmission output circuit 33. Secondly, the outputs of the contact sensor 47 and the limit switch 48 which inherently provide on-off signals are transmitted in series on a signal transmission line 38 by the use of a multiplexor 34 and a transmission output circuit 35. In this way, the large number of signal outputs can be transmitted to the control device by only the two channels of signal transmission lines.

The circuit elements 31-35 in the pre-processing circuit 30 have their operations controlled by a sequencer 36, whereby the various detection signals are delivered to the signal transmission lines 37 and 38 in a predetermined sequence.

FIG. 4(b) shows a control circuit 50 and a microcomputer 70 which constitute part of the control device 7 and which take partial charges of the control of the inspection mechanism portion 10.

The control circuit 50 is divided into a receiver circuit system which deserializes again the series signals transmitted in series from the pre-processing circuit 30, and a servo circuit system which controls the d.c. servomotor 42 of the mechanism portion. Servo circuits 51 consist of five channels 51a-51e in correspondence with the moving control circuits 41a-41e, but for the sake of brevity the connections of signals are illustrated on the channel 51a only. The receiver circuit system includes a circuit 61 which receives the signals from the signal transmission line 37 and which decodes them into parallel signals, and a circuit 62 which receives the signals from the signal transmission line 38 and which decodes them into parallel signals. Among the outputs of the circuit 61, the signal indicative of the status of the potentiometer 44 is transferred to a register 55 in the servo circuit, and the signal indicative of the status of the proximity sensor 22 is transferred to a register 63. On the other hand, the outputs of the circuit 62, that is, the signals from the contact sensor and the limit switch are transferred to registers 64 (only one is indicated for the sake of brevity). These circuit elements have their operations controlled by a sequencer 65. The registers 63 and 64 are connected to a signal bus line 77 of the microcomputer 70, and their contents are utilized for various control processings to be stated later.

The servo circuit 51a is constructed as described below. A register 52 is comprised which receives a movement command value from the micro-computer 70. The command signal is converted by a D/A converter 53 into an analog signal, which is delivered through a servo-amplifier 54 to a signal line 40a as a signal for driving the d.c. servomotor 42 of the moving control circuit 41a. The output signal of the potentiometer indicative of the movement of the motor has been transmitted to the register 55 as already stated, and the output of the register is fed back to a summing circuit 57 via a D/A converter 56.

The micro-computer 70 includes a processor 71, a RAM 72 for storing data, a ROM 73 for storing programs and an arithmetic unit 74 for high-speed operations, and besides, an interface circuit 75 for making possible the association with a separate control circuit 90 which controls the traverse machine 6 etc. As will be stated later, the micro-computer executes the control of the sequence of the inspection jobs, and the storage of measured results on the relative positional relations between the inspection apparatus and the pipe being the object to-be-inspected as well as the arithmetic processings of an inspection work angle etc. based on the stored results.

The video signal transmitted through a signal line 84 from the TV camera 27 is amplified by a video amplifier 85, and projects the image of a vision of inspection on the monitor TV 8.

The operator monitoring the TV screen can adds a change of the control of the inspection apparatus 10 based on the micro-computer 70 by manipulating a control panel 80. A brightness adjusting circuit 81 is also controlled by an output from the control panel 80. An output of the brightness adjusting circuit 81 is applied through a signal line 83 to the light source 27 for illuminating the vision imaged by the inspection head 20, whereby the brightness of the image is adjusted.

The following items are mentioned as points which are especially important in case of automatically executing the visual inspection of the inner surface of a pipe by means of the inspection apparatus having the mechanism and control circuitry as stated above:

(1) The inspection position can be known precisely.

In case of visually inspecting a pipe in a large-size plant, it is unsatisfactory that merely the stained or damaged state of an object surface can be found out, and the position of the stained or damaged part must be known accurately. This is because the position where the stain etc. have been found out is repaired with another equipment after the inspection in some cases, and the progress of the stain etc. needs to be grasped at an inspection after a fixed period in other cases. By way of example, consider a case where the visual inspection head 20 has a rectangular field of vision of fixed dimensions. In case of scanning the inspection head along the inner surface of the cylindrical object under such condition, the inspection head needs to successively move in correspondence with meshed positions (hereinbelow, termed "addresses") corresponding to the size of the field of vision as indicated by broken lines in FIG. 5. Such meshes need to be formed on the basis of the cylindrical pipe itself. Conversely, in case where a predetermined address has been assigned, the inspection head must be positioned to the central part of the mesh corresponding to this address.

(2) The inspection work is executed under the state under which the opposing distance and the opposing angle between the object to-be-inspected and the inspection head are held substantially constant.

In case where the oppposing distance between the inspection head and the object surface has fluctuated, naturally the dimensions of the object stain etc. on the monitor TV set which the operator is monitoring are seen to be difficult. It is apparent that also a change in the opposing angle forms a cause for a similar picture strain.

In the above, the important conditions required for the precise visual inspection have been stated. In case where the large-sized plant or the like is the object to-be-inspected, it is extremely difficult to meet these requirements. The first reason therefor is that the position of the pipe is inaccurate in itself, and the second is that since the traverse means 6 for setting the inspection apparatus into front of the pipe has a very large size, the positioning capability thereof is limited. The visual inspection mechanism accordingly needs a function for correcting a relative set error attributed to the reasons.

Figure 6:
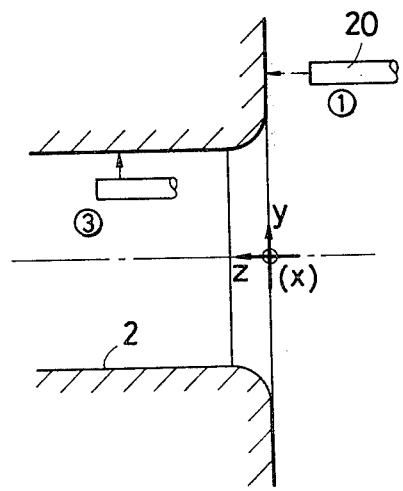
FIGS. 6 and 7 are views for explaining the arrangements of proximity sensors necessary for moving the inspection apparatus to the position of an object to-be-inspected.
Figure 7:
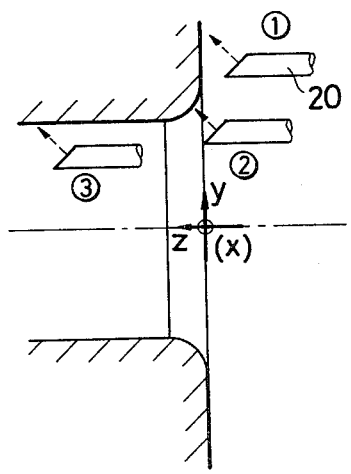

In order to realize such correcting function, the apparatus of this invention utilizes the proximity sensor 22 installed on the inspection head. In this invention, the positional correction is realized with a small number of proximity sensors by object-surface measuring and calculating processings to be stated later, which has a very high practical value. Hereunder, the contents will be described with reference to FIGS. 6 and 7.

First, a method of arranging the proximity sensors will be described. In case of bringing the inspection head 20 near to the pipe and scanning the former at a fixed spacing from the object surface, basically two proximity sensors are required. They are a sensor for measuring a distance to a wall around the pipe in the direction of a broken-line arrow when the inspection head 20 is in a state ① in FIG. 6, and a sensor for measuring a distance to the inner surface of the pipe in the direction of a broke-line arrow under a state ③. However, when an oblique proximity sensor is arranged on the fore end of the inspection head as illustrated by broken lines in FIG. 7, the above-mentioned distance measurements in the two directions can be made with the single sensor, and furthermore, the measurement of a distance to a corner part where the wall shifts to the inner surface is also possible as shown at ② in FIG. 7. The mechanism shown in FIG. 2 is provided with the proximity sensor 22a having such function, and besides the proximity sensor 22b for detecting the inner surface of the pipe, whereby the detection of the relative inclination of the inspection head to the axial direction of the pipe becomes possible anew.

There will now be described the control procedures of the object-surface measurement utilizing the proximity sensors in such arrangement and construction and the visual inspection work employing a calculated result based thereon.

FIIG. 8 indicates the fundamental contents of the inspection work control. First of all, the inspection apparatus 10 is set to the position in front of the pipe being the object to-be-inspected by the traverse machine 6 (block ST1). At this time, the inspection head 20 is in the state in which it withdraws inside the protective cover 16a shown in FIG. 2.

Subsequently, the control proceeds to block ST2 to execute the operation of measuring the object position. The content of the measuring operation is as follows.

The sliding shaft 15 of the mechanism portion is advanced to bring the inspection head 20 near to the wall around the pipe, and the position of the wall is examined with the proximity sensor. This corresponds to the state ① in FIG. 6 or 7, and equivalently measures the position of the Z-directional origin of the pipe. As a result, the position of the sliding shaft 15 which corresponds to the Z-directional address, for example, 101-*a* or 102-*a* in the meshes shown in FIG. 5 can be stipulated.

In case where the position of the object wall is abnormally distant in such measuring operation, the control proceeds to decision block ST3. If the position is substantially normal, the operation of measuring the position of the inner surface of the pipe is successively executed. That is, the sliding shaft is further advanced to insert the inspection head into the pipe in the form in which the inspection head goes along the corner part as illustrated at ② in FIG. 7, or in the form in which the inspection head is moved near to the axis of the object pipe by the extending-and-shortening shaft 12 of the mechanism portion. The inspection head 20 is thereafter moved along a circumferential path under the state ③ in FIG. 6 or 7, that is, under the state under which the inspection head is brought near to a position at a fixed distance from the inner surface of the pipe and under which the distance is held. At this time, the position of the center axis $Z_1$ of the pipe can be known from the angle of rotation of the revolving shaft 11 and the position of movement of the extending-and-shortening shaft 12.

Figure 9:
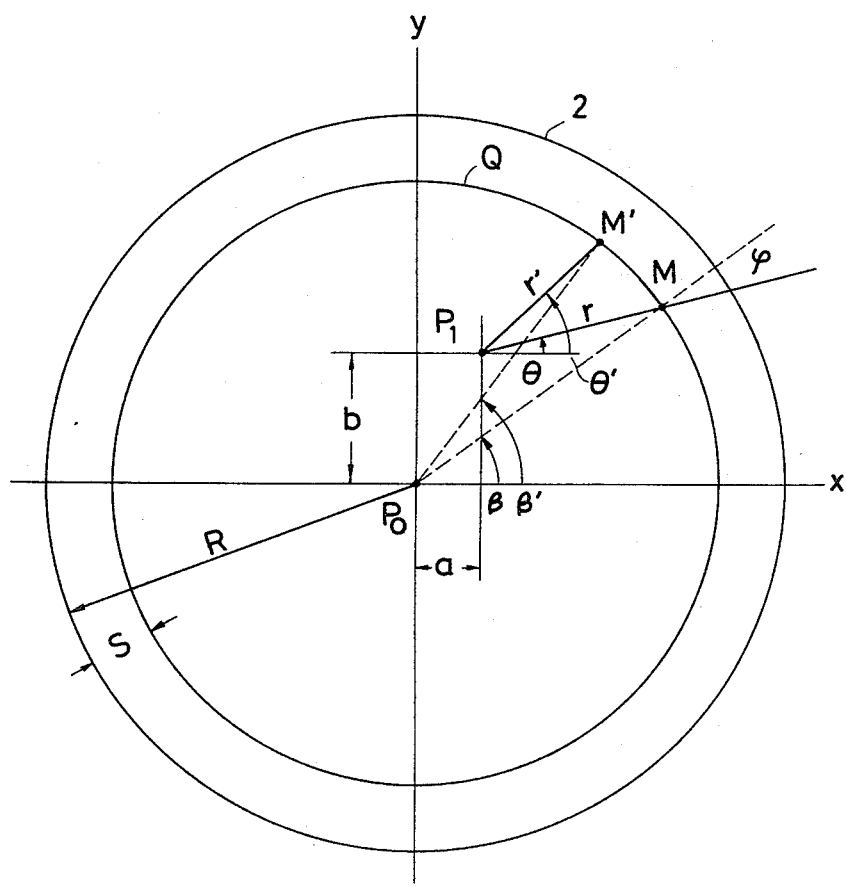
FIG. 9 is a diagram for explaining a method of calculating the amount of positional deviation between the center axis of a pipe being an object to-be-inspected and the operating center axis of the inspection apparatus.

The operation of measuring the position of the inner surface of the pipe will be further explained with reference to FIG. 9. It is now assumed that the center axis of the revolving shaft 11 of the inspection apparatus line at a position $P_1$ which deviates a in the x-axial direction and b in the y-axial direction from a position $P_o$ of the center axis $Z_1$ of the pipe having a radius R.

While controlling the extending-and-shortening shaft 12 in response to the output signal of the proximity sensor 22a or 22b, the angle of the revolving shaft 11 from the horizontal position is changed from $\theta$ to $\theta'$. Thus, the inspection head 20 is moved from a position M to a position M' with a fixed distance S from the pipe wall 2 held. Supposing that the positions M and M' of the inspection head at this time define angles $\beta$ and $\Gamma'$ respectively with the x-axis in the x-y coordinate system whose origin is the central position $P_o$ of the pipe, and that the length of the extending-and-shortening shaft 12 has changed from r to r', and values a and b are obtained from the following equations:

$$a = (R-S) \cos \beta - r \cos \theta \quad (1)$$

$$b = (R-S) \sin \beta - r \sin \theta \quad (2)$$

where $$\beta = \tan^{-1}\left(-\frac{r\cos\theta - r'\cos\theta'}{r\sin\theta - r'\sin\theta'}\right) + \frac{1}{2}\cos^{-1}\left\{\frac{2(R-S)^2 - (r^2 + r'^2) + 2rr'\cos(\theta - \theta')}{2(R-S)^2}\right\} \quad (3)$$

Accordingly, the rotational angle $\theta$ of the revolving shaft 11 necessary for positioning the inspection head to any desired angle $\beta$ from the center $P_o$ of the pipe is given by:

$$\theta = \tan^{-1}\left(\frac{(R-S)\sin\beta - b}{(R-S)\cos\beta - a}\right) \quad (4)$$

The angle $\phi$ defined between straight lines $P_o$—M and $P_1$—M becomes:

$$\phi = \beta - \theta \quad (5)$$

In case where, as the result of the above measurement of the position of the inner surface of the pipe, the relative distance between the revolving shaft 11 and the pipe 2 has been found to be abnormally great, it is decided that the inspection work is impossible in that condition, and a correction for the position of the traverse machine is requested (block ST3).

Figure 5:
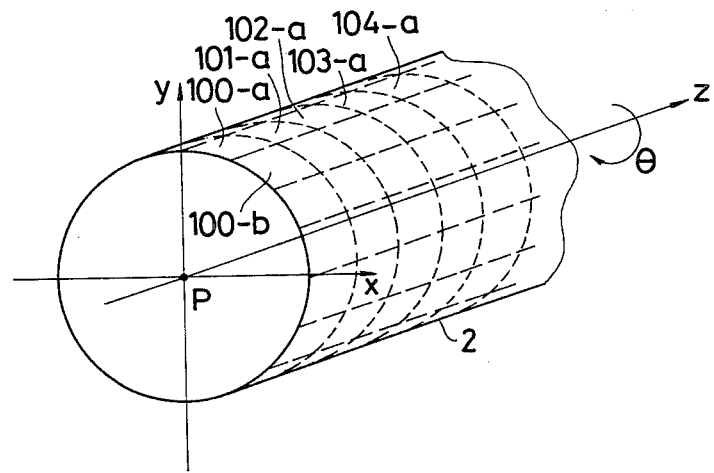
FIG. 5 is a diagram for explaining an example of setting of inspection addresses which are set in the form of meshes on the circumferential surface of a pipe to-be-inspected.

In case where the inspection has been decided to be possible, the control proceeds to block ST4, and inspection head movement position data necessary for automatically inspecting precisely the meshed addresses in FIG. 5 are indexed by calculations. In the succeeding block ST5, the driving shafts of the inspection apparatus are controlled on the basis of the calculated data, and the inspection head is sequentially moved to the respective addresses of the object surface divided into the meshes.

Figure 10:
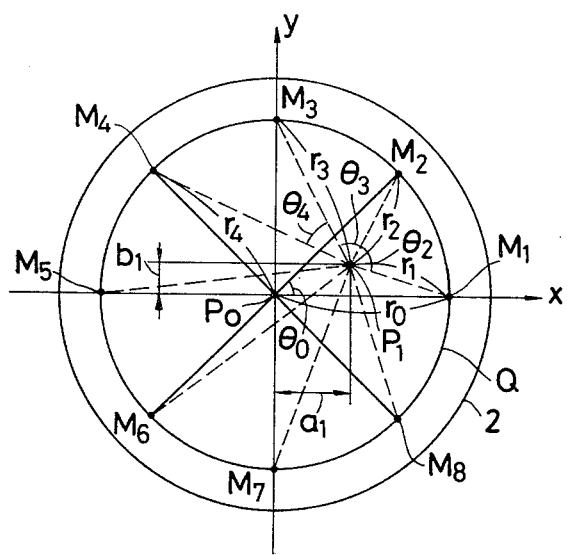
FIGS. 10 and 11 are diagrams for explaining control procedures for drive shafts of an inspection head-positioning mechanism in the case of visually inspecting the inner surface of a pipe at equal intervals.

Here, the content of the indexing of the inspection position in the block ST4 will be further described with reference to FIG. 10. In FIG. 10, numeral 2 indicates the position of the inner surface of the pipe to be inspected, and letter Q indicates the path along which the inspection head 20 moves during the inspection in the circumferential direction. For the sake of brevity, let's consider a case where the meshes consist of eight addresses in the circumferential direction. If, at this time, the center of the revolving shaft of the inspection apparatus is coincident with the center $P_0$ of the pipes, then in case of moving the inspection head along $M_1 \rightarrow M_2 \rightarrow M_3$ in correspondence with the eight addresses the revolving shaft 11 may hold a fixed angle $\theta_0$ (45° in this case) and the extending-and-shortening shaft 12 may hold a fixed position $r_0$. However, in case where the center of the revolving shaft 11 has been set at a position $P_1$ on account of a deviation in the stop position of the traverse machine, the revolving shaft must be varied into $\theta_2$ and $\theta_3$ and the extending-and-shortening shaft into $r_2$ and $r_3$ for the shift from $M_1$ to $M_2$ and then $M_3$. The operating positions of the revolving shaft corresponding to the respective addresses in this manner can be calculated from Equations (4) and (5) on the basis of the positional deviations a and b of $P_1$ relative to $P_0$ in accordance with the apparatus of this invention. In addition, the magnitudes of the deviations a and b can be calculated with Equations (1), (2) and (3) from the circumferential measurement results described before. The circumferential measurement need not always be made over the whole periphery of the section of the pipe. When the structure 3 as shown in FIG. 3(*c*) is disposed within the pipe and the positional relation between it and the pipe is known in advance, the measurement of position around the structure can be sometimes substituted for the circumferential measurement. Such circumferential measurement work need not always be executed under the condition under which the proximity sensor is at a fixed distance from the object surface. It is also allowed to adopt a method wherein the revolving shaft is rotated with the extending-and-shortening shaft held in a fixed state, to know the relationship between the rotational angle and the distance information of the proximity sensor.

Figure 11:
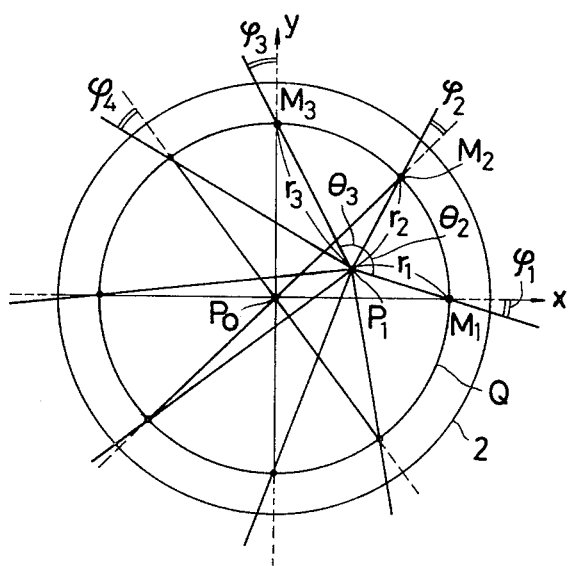

When the positional deviation of $P_1$ relative to $P_0$ is great, the precise visual inspection is impossible with only the correcting operation resorting to the revolving shaft 11 and the extending-and-shortening shaft 12 as explained with reference to FIG. 10. This is because the angle of the viewing direction of the inspection head deviates successively as $\phi_2$ and $\phi_3$ relative to the target meshes as illustrated in FIG. 11. Accordingly, the deviation angle is calculated, and in order to turn the angle of the viewing direction towards the central position of the mesh, the rotating shaft 14 shown in the mechanism portion of FIG. 2 is utilized in the apparatus of this invention.

As stated above, in the inspection apparatus according to this invention, the position of the pipe being the object to-be-inspected is measured by the proximity sensors previously to the automatic inspection operation, and the propriety of the execution of the visual inspection work is decided on the basis of the measurement, and further, in case where the execution is possible, the operating positions of the respective driving shafts for making possible the precise automatic inspection along the meshed addresses with reference to the pipe can be calculated. Thus, the subsequent automatic inspection can be carried out at high speed, and even when in the course of the automatic inspection (block ST5) a manual operation by the operator intervenes temporarily (block ST6), the inspection head can be precisely returned to a necessary address again. Of course, it is possible to compensate for an insufficient accuracy of calculation by feeding back the output of the proximity sensor in the process of the automatic inspection, or to correct the indexed positions of the respective shafts already calculated and stored if necessary.

On the other hand, as stated in the description taken with reference to FIG. 3, under the condition under which the relative inclination between the axis $Z_1$ of the pipe and the reference axis of the inspection mechanism (for example, the revolving shaft) is not negligible, the correcting operation employing the swinging shaft 13 may be conducted. A correction angle necessary therefor can be derived from the difference of the outputs of the two proximity sensors for measuring the inner surface of the pipe at the circumferential measurement, or from the results of two circumferential measurements at different positions of the sliding shaft in case where only one proximity sensor is provided.

Figure 8:
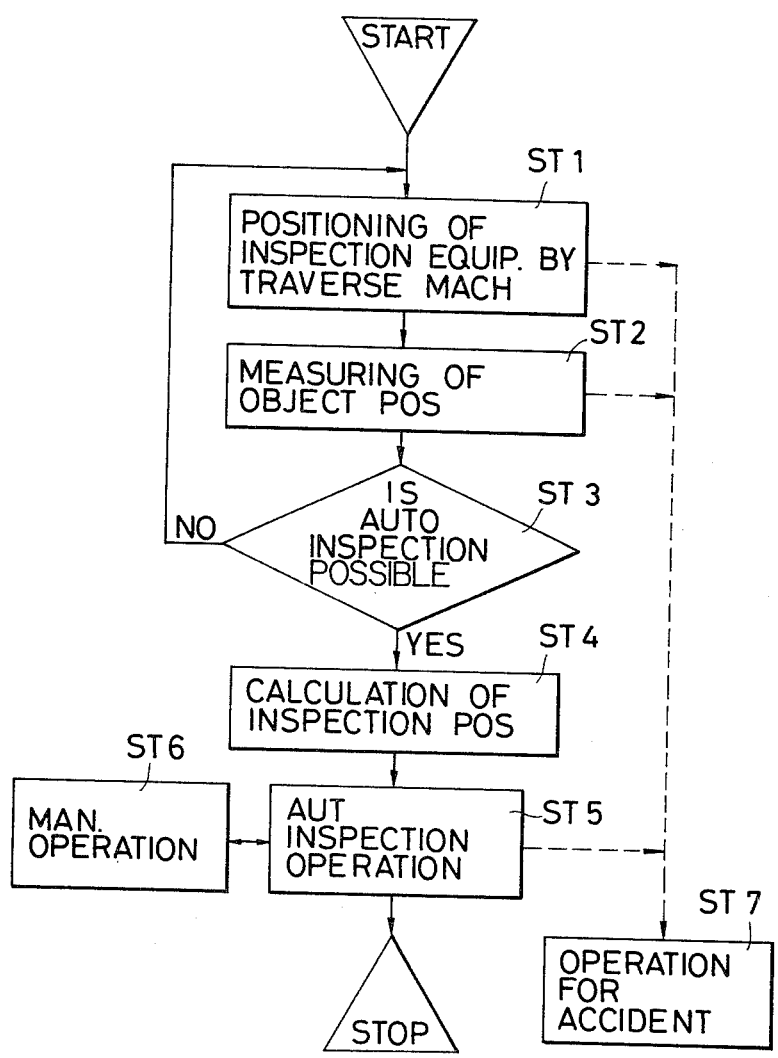
FIG. 8 is a flow chart showing the basic operating procedures of the inspection apparatus according to this invention.

In FIG. 8, block ST7 is an abnormality processing routine. When, under the operation of the inspection apparatus, a part of the apparatus has touched an obstacle or an abnormality has been detected in the mechanical system or electric system, the operation of the inspection apparatus is stopped and a processing of alarming the operator is executed in this routine.

Figure 12:
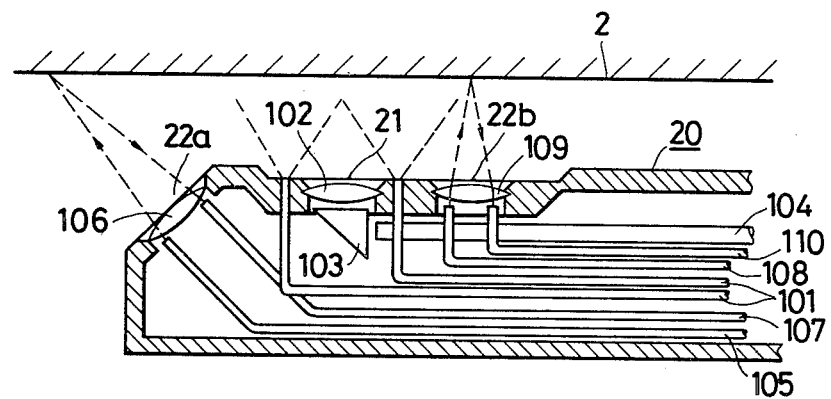
FIG. 12 is a sectional view showing an example of an inspection head provided with optical proximity sensors.

FIG. 12 shows an inspection head 20 provided with optical proximity sensors according to which information on a proximate distance to the object are transmitted together with an inspection image signal to the control device disposed at the remote spot, thereby permitting the distance information to be displayed on the monitor TV set.

Referring to the figure, an optical system 21 for receiving an inspection image is composed of a light guide 101 for transmitting illumination light from a light source 26 and illuminating the field of vision to-be-inspected, a lens 102, a prism 103, and an image guide 104 for transmitting to a TV camera 27 an inspection image received through the lens and the prism.

A proximity sensor 22a is composed of a light guide 105 for transmitting illumination light from the light source 26 and projecting slit light (or spot light) onto the wall, a lens 106, and an image guide 107 for transmitting to the TV camera that image of a space illuminated by the slit light which is received through the lens 106.

Likewise to the proximity sensor 22a, a proximity sensor 22b is composed of a light guide 108, a lens 109 and an image guide 110.

The image guides 104, 107 and 110 have rectangular light-receiving surfaces, and transmit scenes of rectangular fields of vision to the TV camera.

Figure 13:
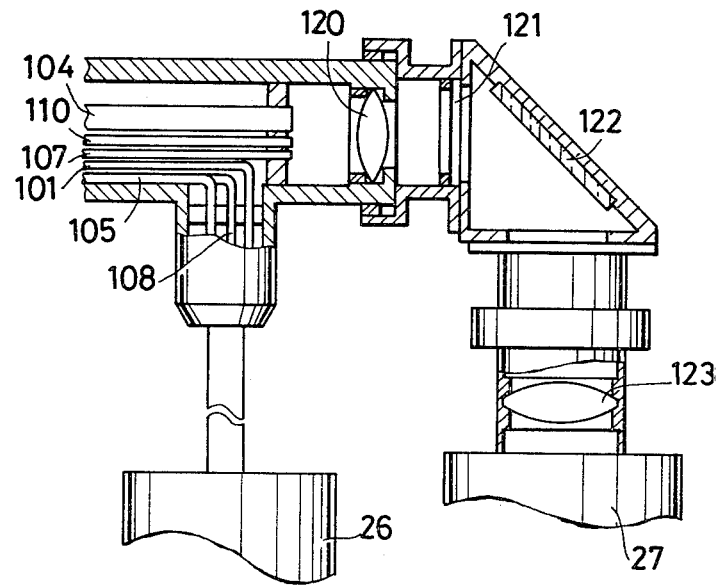
FIG. 13 is a view showing a coupling portion between the terminal end of an image guide of the inspection head in FIG. 12 and a TV camera.

FIG. 13 is a constructional view of the coupling portion between the image guides above described and the TV camera 27. The images which appear at the end faces of the three image guides 104, 107 and 110 are received onto the photoelectric screen of the TV camera 27 through an ocular lens 120, a filter 121, a reflector 122 and an adaptor lens 123. The light guides 101, 105 and 108 are connected to the light source 26.

Figure 14:
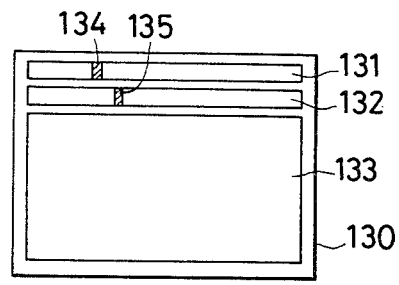
FIG. 14 is a view for explaining a TV picture obtained with the inspection head in FIG. 12.

Shown in FIG. 14 is an output image 130 from the TV camera 27 which is obtained on the monitor TV set 8 owing to the above construction. Numeral 131 designates a region of the image of the proximity sensor 22a delivered from the image guide 107, numeral 132 a region of the image of the proximity sensor 22b delivered from the image guide 110, and numeral 133 a region of the inspection image delivered from the image guide 104. Numerals 134 and 135 indicate positions of illumination patterns which are formed into a specified shape on the wall by the beams projected from the respective light guides 106 and 108 and which are slit-like bright patterns in this case. The positions 134 and 135 of the slit patterns appear at positions on the TV screen differing in dependence on the distance between the inspection head 20 and the wall 2. Accordingly, the operator monitoring the monitor TV set can know the positional relationship between the inspection head 20 and obstacles in front and by the side thereof from the positions of the slit patterns appearing in the image regions 131 and 132.

Figure 15:
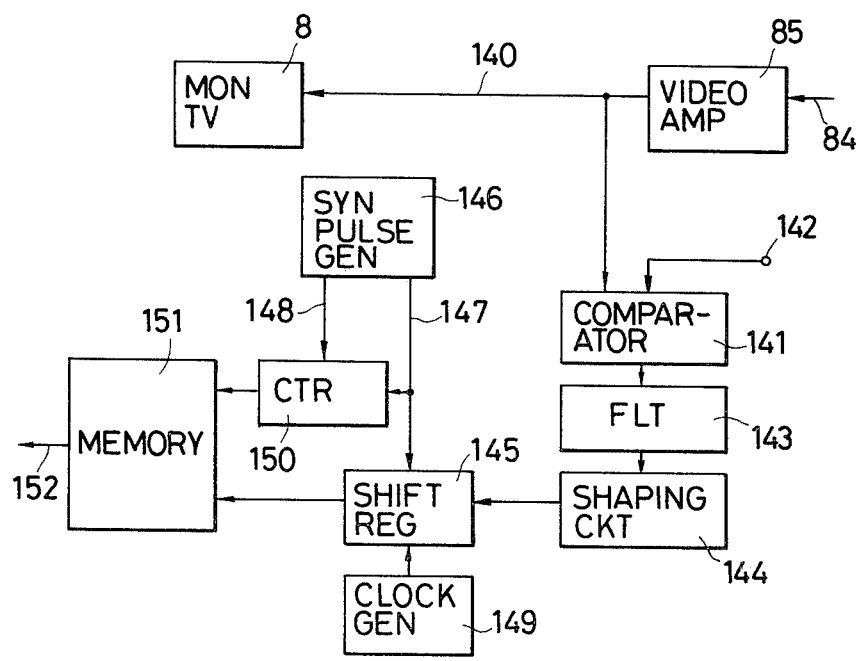
FIG. 15 is a diagram showing an example of a circuit for separating proximate distance data from video signals in the inspection apparatus which employs the inspection head in FIG. 12.

In case of using the optical proximity sensors described above, the distance data to be given to the micro-computer 70 can be obtained from a video signal by means of a circuit shown in FIG. 15.

The video signal 84 is amplified by a video amplifier 85, an output signal 140 of which is applied to a comparator 141. A predetermined threshold signal is applied to the other input terminal of the comparator 141. The comparator provides an output only when the level of the video signal corresponding to the slit pattern 134 or 135 previously stated has exceeded the threshold. The output of the comparator 141 is passed through a filter 143 and a shaping circuit 144 into an "on-off" signal with a noise component removed, which is applied to a shift register 145. After being reset by a horizontal synchronizing pulse 147 provided from a synchronizing pulse generator 146, the shift register 145 is driven by a clock pulse provided from a clock generator 149. As a result, binary data which indicate the existing position of the on-off signal on one horizontal scanning line are provided from the shift register 145 and are stored into a random access memory 151. Further, the horizontal synchronizing pulse 147 drives a counter 150 which is reset by a vertical synchronizing pulse 148 provided from the synchronizing pulse generator 146. An output from the counter 150 indicates the number of horizontal scanning lines, and is stored into the memory 151.

By the above processing, which horizontal scanning lines and which parts in the lines within the picture regions 131 and 132 allotted to the proximity sensors the slit-like patterns lie in are stored into the random access memory 151. An output 152 from the memory 151 is loaded into the micro-computer circuit 70 for controlling the servo circuit 50, as may be needed. The slit patterns indicative of the proximity distances have a fixed width in the horizontal direction, and the intermediate position of the width can be regarded as the relative distance to the object surface. In this case, reflection positions indicated on a plurality of scanning lines may well be averaged and regarded as the relative distance to the object surface. These disposals can be executed at will by the calculations of the micro-computer 70 utilizing the stored results of the memory 151.

Since, in the present embodiment, the proximate distance information are transmitted to the micro-computer through the memory 151, the register 63 shown in FIG. 4(b) is unnecessary.

The inspection apparatus according to this invention can employ various kinds of proximity sensors in the inspection head portion. However, in case where as described with reference to FIGS. 12 to 15 the optical proximity sensors are disposed in the inspection head portion and the proximity distance information optically received are applied to the TV camera for the inspection image so that the control device installed on the remote spot may separate the distance information from the video signal and control the positioning mechanism, the constituent parts of the proximity sensors can be made small in size and light in weight, and the proximity sensor information can be transmitted to the control device at the remote spot by means of the transmission cable for TV originally required for the visual inspection and can also be displayed on the TV monitor for the visual inspection by the operator.

In consequence, there are such advantages that the operator who inspects the inspection image can check the abnormal approach of the inspection head to the object surface ascribable to any abnormality of the proximity sensor system or any accident of another part and can take a measure such as the emergency stop of the apparatus, and that when the operator causes the inspection head to approach the object surface by the manual operation, the degree of proximity can be visually checked.

In the above, the content of this invention has been described on the inspection of the inner surface of the pipe having the circular section. It is to be understood, however, that the principle of this invention is also applicable to pipes and vacant spaces having sections other than the circular ones or to outer surfaces of the pipes.

What we claim is:

1. Apparatus for inspecting pipes in a plant, comprising:
    an inspection head portion which is provided with an optical system for receiving an image of an inner surface of the pipe being an object to-be-inspected,
    means for converting the inspection image received into said optical system, into electrical video signals,
    at least one proximity sensor which is disposed in said inspection head portion in order to detect a relative distance between said inspection head portion and the proximate object,
    a positioning mechanism which is made up of a plurality of driving shafts for moving said inspection head portion,
    control means capable of programmed operation, for guiding said inspection head portion from an initially set position outside the pipe to an inspection position inside said pipe and moving said inspection head portion along a track set with reference to the object to-be-inspected and without contact with said object to-be-inspected, and for driving said positioning mechanism in a predetermined operation sequence programmed in advance in response to an output signal from said proximity sensor, and
    image processing means situated at a position remote from said inspection head portion and for reconstructing the inspection image from the video signal.

2. Apparatus for inspecting pipes in a plant as defined in claim 1, wherein said positioning mechanism comprises a first driving shaft which is elongate and which is movable in a direction of a center axis of the pipe, a second driving shaft which moves said first driving shaft in a direction orthogonal to said center axis of said pipe, and a third driving shaft which revolves said second driving shaft, said inspection head portion being situated at a front end part of said first driving shaft.

3. Apparatus for inspecting pipes in a plant as defined in claim 2, wherein said first driving shaft is rotatable.

4. Apparatus for inspecting pipes in a plant as defined in claim 1, 2 or 3, wherein at least one of the proximity sensors has outer information receiving means directed obliquely frontwards so as to detect a relative distance to the object in this direction.

5. Apparatus for inspecting pipes in a plant as defined in claim 1, 2 or 3, wherein:
    the proximity sensor disposed in said inspection head portion consists of first means for projecting light in a specified sectional shape towards the object to-be-inspected, and optical second means for receiving an image of a region including an illumination pattern in a specified shape formed on said object to-be-inspected by said light and for applying said image to the conversion means,
    said image processing means includes means for detecting a position of said illumination pattern contained in the video signal, and
    said control means controls said positioning mechanism on the basis of a signal indicative of said position of said illumination pattern delivered from the detection means.

6. Apparatus for inspecting pipes in a plant as defined in claim 5, wherein said first means includes at least one proximity sensor which projects light in a specified sectional shape obliquely frontwards.

7. A method for controlling inspection apparatus which is set into front of a position of an object to-be-inspected by a traverse machine in order to inspect pipes in a plant,
    said inspection apparatus having:
    a positioning mechanism having a first driving shaft which is elongate and rotatable and which moves in a direction of a center axis of the pipe, a second driving shaft which moves said first driving shaft in a direction orthogonal to said center axis, and a third driving shaft which revolves said second driving shaft; and an inspection head portion which is situated at a front end part of said first driving shaft and which is provided with an optical system for receiving an image of the object to-be-inspected, and at least one proximity sensor for detecting a relative distance between said inspection head portion and said object;

the control method comprising:

the step of advancing said first driving shaft and inserting said inspection head portion into the pipe being said object to-be-inspected;

the step of revolving said third driving shaft a predetermined angle while moving said second driving shaft in response to an output of said proximity sensor so as to hold constant a distance between said inspection head portion and an inner surface of said pipe, thereby to detect a positional deviation amount between said third driving shaft and said center axis of said pipe; and the inspection image input step of controlling a revolution angle of said third driving shaft in response to the positional deviation amount while moving said second driving shaft in response to the output of said proximity sensor;

whereby inspection images are picked up at equal intervals in a circumferential direction of said pipe.

8. A method of controlling inspection apparatus as defined in claim 7, wherein in the inspection image input step, a rotational amount of said first driving shaft is controlled in response to the positional deviation amount between said third driving shaft and said center axis of said pipe and the revolution amount of said third driving shaft, whereby said optical system of said inspection head portions always faces perpendicularly to said inner surface of said pipe at the respective inspection positions.

* * * * *